(12) United States Patent
Stivland et al.

(10) Patent No.: US 6,712,807 B2
(45) Date of Patent: Mar. 30, 2004

(54) CATHETER HAVING IMPROVED FLEXIBILITY CONTROL

(75) Inventors: Timothy M. Stivland, Plymouth, MN (US); Elias A. Khoury, Champlin, MN (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/087,338

(22) Filed: Feb. 28, 2002

(65) Prior Publication Data

US 2002/0128596 A1 Sep. 12, 2002

Related U.S. Application Data

(63) Continuation of application No. 09/208,335, filed on Dec. 9, 1998, now abandoned.

(51) Int. Cl.$^7$ .................... A61M 25/00; A61M 25/01; A61M 25/02; A61M 25/04; A61M 24/06; A61M 25/08; A61M 25/082; A61M 25/085; A61M 25/088; A61M 25/09; A61M 25/095; A61M 25/098; A61M 25/18; A61M 5/178

(52) U.S. Cl. .................. 604/524; 604/528; 604/537; 604/164.13

(58) Field of Search .............. 604/524, 164.13, 604/510, 525, 528, 530, 531, 532, 533–537; 600/434

(56) References Cited

U.S. PATENT DOCUMENTS

| | | | |
|---|---|---|---|
| 2,687,131 A | 8/1954 | Raiche | 123/349 |
| 2,936,760 A | 5/1960 | Gants | 123/349 |
| 3,225,762 A | 12/1965 | Guttman | 128/214 |
| 3,884,242 A | 5/1975 | Bazell et al. | 128/351 |
| 4,044,765 A | 8/1977 | Kline | 128/214.4 |
| 4,289,128 A | 9/1981 | Rüsch | 128/207.15 |
| 4,468,224 A | 8/1984 | Enzmann et al. | 604/247 |

(List continued on next page.)

FOREIGN PATENT DOCUMENTS

| | | |
|---|---|---|
| EP | 0 344 530 A1 | 12/1989 |
| EP | 0 365 993 A1 | 5/1990 |

(List continued on next page.)

OTHER PUBLICATIONS

Paul G. Yock, U.S. patent application Ser. No. 852,197, Filed Apr. 15, 1986.

(List continued on next page.)

*Primary Examiner*—Brian L. Casler
*Assistant Examiner*—Catherine S. Williams
(74) *Attorney, Agent, or Firm*—Crompton, Seager & Tufte LLC

(57) ABSTRACT

Catheters having improved flexibility control, which can be provided by a slidable core wire disposed within the catheter and by shafts formed from segmented spine wires disposed within polymeric tubes. One catheter is an angioplasty catheter including an axially slidable core wire disposed within an inflation lumen, and having a pressure seal disposed about the core wire extending proximally from the catheter proximal end. The slidable core wire can provide a varying degree of stiffness to the catheter. The catheter can have greater stiffness when the core wire is axially distally extended and less stiffness when the core wire is retracted. One catheter has a shaft including a spine wire or stiffening element within an outer polymeric tube. The spine wire can include multiple segments having alternating wide and narrow segments, with the wide segments contacting the outer tube and contributing stiffness to the shaft and with the narrow segments contributing flexibility to the shaft. In one catheter, the wide segments have apertures therethrough allowing fluid flow through the polymeric tube. In one catheter, the wide segments have distally increasing inter-segment distance, providing distally increasing flexibility.

18 Claims, 1 Drawing Sheet

U.S. PATENT DOCUMENTS

| | | | | |
|---|---|---|---|---|
| 4,597,755 | A | 7/1986 | Samson et al. | 604/96 |
| 4,601,713 | A | 7/1986 | Fuqua | 604/280 |
| 4,662,368 | A | 5/1987 | Hussein et al. | 128/303.1 |
| 4,705,507 | A | 11/1987 | Boyles | 604/101 |
| 4,719,924 | A | 1/1988 | Crittenden et al. | 128/772 |
| 4,748,982 | A | 6/1988 | Horzewski et al. | 128/344 |
| 4,762,129 | A | 8/1988 | Bonzel | 128/344 |
| 4,771,777 | A | 9/1988 | Horzewski et al. | 128/344 |
| 4,798,598 | A | 1/1989 | Bonello et al. | 604/280 |
| 4,820,349 | A | 4/1989 | Saab | 128/344 |
| 4,824,435 | A | 4/1989 | Giesy et al. | 604/49 |
| 4,838,268 | A | 6/1989 | Keith et al. | 128/344 |
| 4,846,174 | A | 7/1989 | Willard et al. | 128/344 |
| 4,877,031 | A | 10/1989 | Conway et al. | 128/344 |
| 4,881,547 | A | 11/1989 | Danforth | 128/344 |
| 4,896,670 | A | 1/1990 | Crittenden | 606/194 |
| 4,906,241 | A | 3/1990 | Noddin et al. | 606/194 |
| 4,917,088 | A | 4/1990 | Crittenden | 606/194 |
| 4,921,478 | A | 5/1990 | Solano et al. | 604/53 |
| 4,928,693 | A | 5/1990 | Goodin et al. | 128/637 |
| 4,940,062 | A | 7/1990 | Hampton et al. | 128/772 |
| 4,943,278 | A | 7/1990 | Euteneuer et al. | 604/96 |
| 4,944,745 | A | 7/1990 | Sogard et al. | 606/194 |
| 4,946,466 | A | 8/1990 | Pinchuk et al. | 606/194 |
| 4,953,553 | A | 9/1990 | Tremulis | 128/637 |
| 4,976,690 | A | 12/1990 | Solar et al. | 604/96 |
| 4,976,720 | A | 12/1990 | Machold et al. | 606/194 |
| 4,988,356 | A | 1/1991 | Crittenden et al. | 606/194 |
| 4,994,032 | A | 2/1991 | Sugiyama et al. | 604/96 |
| 4,998,917 | A | 3/1991 | Gaiser et al. | 604/96 |
| 4,998,923 | A | 3/1991 | Samson et al. | 606/194 |
| 5,032,113 | A | 7/1991 | Burns | 604/96 |
| 5,034,001 | A | 7/1991 | Garrison et al. | 604/53 |
| 5,035,686 | A | 7/1991 | Crittenden et al. | 604/96 |
| 5,035,705 | A | 7/1991 | Burns | 606/194 |
| 5,040,548 | A | 8/1991 | Yock | 178/848 |
| 5,042,985 | A | 8/1991 | Elliott et al. | 606/192 |
| 5,047,045 | A | 9/1991 | Arney et al. | 606/194 |
| 5,050,606 | A | 9/1991 | Tremulis | 128/637 |
| 5,057,120 | A | 10/1991 | Farcot | 606/194 |
| 5,061,273 | A | 10/1991 | Yock | 606/194 |
| 5,102,390 | A | 4/1992 | Crittenden et al. | 604/96 |
| 5,102,403 | A | 4/1992 | Alt | 604/280 |
| 5,112,304 | A | 5/1992 | Barlow et al. | 604/96 |
| 5,156,594 | A | 10/1992 | Keith | 604/96 |
| 5,169,386 | A | 12/1992 | Becker et al. | 604/49 |
| 5,176,637 | A | 1/1993 | Sagae | 604/96 |
| 5,180,367 | A | 1/1993 | Kontos et al. | 604/101 |
| 5,242,396 | A | 9/1993 | Evard | 604/96 |
| 5,346,505 | A | 9/1994 | Leopold | 606/194 |
| 5,382,238 | A | 1/1995 | Abrahamson et al. | 604/170 |
| 5,395,332 | A | 3/1995 | Ressemann et al. | 604/96 |
| 5,425,711 | A | 6/1995 | Ressemann et al. | 604/96 |
| 5,449,343 | A | 9/1995 | Samson et al. | 604/96 |
| 5,468,225 | A | 11/1995 | Teirstein | 604/102 |
| 5,545,138 | A | 8/1996 | Fugoso et al. | 604/102 |
| 5,643,209 | A | 7/1997 | Fugoso et al. | 604/96 |
| 5,702,439 | A | 12/1997 | Keith et al. | 604/96 |
| 5,728,067 | A | 3/1998 | Enger | 604/102 |
| 5,807,328 | A | 9/1998 | Briscoe | 604/96 |
| 6,475,187 | B1 * | 11/2002 | Gerberding | 604/102.02 |

FOREIGN PATENT DOCUMENTS

| | | |
|---|---|---|
| EP | 0 368 523 A2 | 5/1990 |
| EP | 0 380 873 B1 | 5/1990 |
| EP | 0 380 873 A2 | 8/1990 |
| EP | 0 380 873 A3 | 8/1990 |
| EP | 0 830 870 A1 | 3/1998 |
| SU | 1251-914 A | 8/1986 |
| SU | 627828 | 10/1988 |
| WO | WO 89/04686 | 6/1989 |
| WO | WO 95/24236 | 9/1995 |

OTHER PUBLICATIONS

"USCI Lo Profile II Balloon Dilatation Catheters," C.R. Card, Inc. 1987.

"Until Someone Does It, No One Thinks It Can Be Done," C.R. Bard, Inc., 1988.

Schneider–Shiley, brochure entitled *Monorail–Bonzel Coronary Dilatation System*, published on date even with or prior to Nov. 23, 1994.

*Monorail–Piccolino*, Flyer, Oct., 1988.

*ACS RX™ Dilatation Catheters*, Flyer, Mar., 1989.

*Balloon Catheters for Percutaneous Insertion Into the Vascular System*, Björn Nordenström, Mar. 2, 1962.

"New Instruments for Catheterization and Angiocardiography," Björn Nordenström, Jul.–Dec. 1965 Issue of *Radiology*.

* cited by examiner

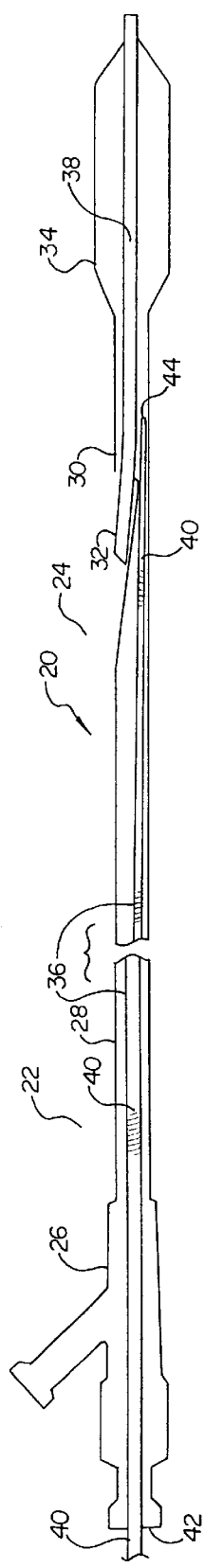
*Fig. 1*
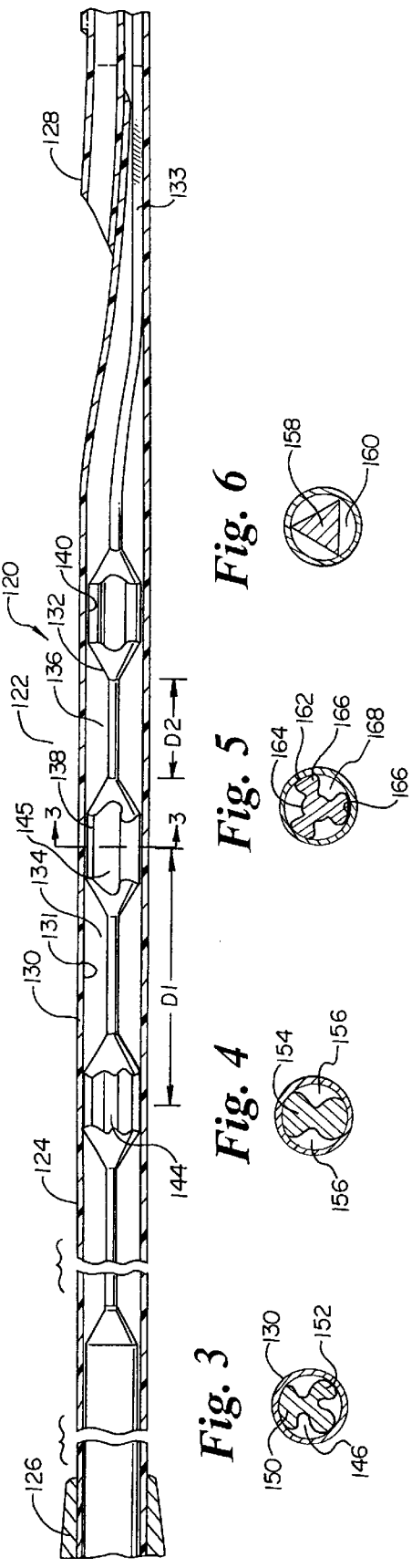
*Fig. 2*
*Fig. 3*
*Fig. 4*
*Fig. 5*
*Fig. 6*

CATHETER HAVING IMPROVED FLEXIBILITY CONTROL

This is a continuation of application Ser. No. 09/208,335, filed Dec. 9, 1998 now abandoned.

FIELD OF THE INVENTION

The present invention relates generally to medical devices. More specifically, the present invention relates to catheters having improved flexibility control. In particular, the present invention includes angioplasty catheters having a slidable core wire disposed within and catheter shafts including a spine wire disposed within a polymeric tube.

BACKGROUND OF THE INVENTION

Angioplasty procedures have gained wide acceptance in recent years as efficient and effective methods for treating types of vascular disease. In particular, angioplasty is widely used for opening stenoses in the coronary arteries and is used for treating stenoses in other vascular regions.

One widely used form of angioplasty makes use of a dilatation catheter which has an inflatable balloon at the distal end and a guide wire lumen within at least a portion of the catheter shaft. Typically, a guide wire is inserted through the vascular system to a position near the stenoses, leaving a proximal portion of the guide wire extending from the patient. The proximal guide wire portion is threaded through the dilatation catheter guide wire lumen and the dilatation catheter advanced through the vascular system over the guide wire to the position near the stenoses. The treating physician manipulates the dilatation catheter until the balloon is positioned across the stenoses. The balloon is then inflated by supplying fluid under pressure through an inflation lumen in the catheter to the balloon. The inflation of the balloon widens the lumen through the stenosed area by pressing the inflating balloon wall against the lesion inside wall.

Flexibility, torqueability, and pushability are important properties in catheter design. Flexibility relates to the ability of the catheter to track through tortuous vessels, particularly through smaller secondary and tertiary coronary vessels. Torqueability refers to the ability to transmit torque from the proximal end to the distal end of the catheter. Treating physicians often require the ability to rotate a curved distal catheter end by rotating the proximal catheter end extending from the patient's body. Rotating the catheter distal end allows the distal tip to be pointed toward a vessel opening, such as a coronary artery ostium. Pushability relates to the ability to transmit lateral force along the catheter without buckling. Flexibility, torqueability, and pushability sometimes conflict as design goals, with one or more being of predominant importance for a given region of a catheter. For example, pushability may be of more importance in the proximal region of a catheter, which may be required to push the distal remainder of the catheter. For example, flexibility may be of more importance in the distal region, which may be required to track tortuous vessel paths having small inside diameters. It may be desirable for catheter flexibility, and other properties, to be varied along the catheter length. What would be desirable is a catheter having varied flexibility along its length. A catheter having flexibility varied with time would also be desirable.

SUMMARY OF THE INVENTION

The present invention includes catheters having improved flexibility control. Some embodiments of the invention have movable core wires slidably disposed within lumen within the catheter shaft. One group of catheters is angioplasty catheters having a core wire slidably disposed within an inflation lumen. One angioplasty catheter includes a pressure seal disposed about the portion of core wire extending proximally from the catheter. In use, one angioplasty catheter having the movable core wire and seal can have the core wire alternately advanced and retracted during different stages of catheter insertion and angioplasty. The core wire can be advanced to enhance stiffness when pushability in a given catheter region is desired, and retracted when flexibility in a given region is desired.

One group of catheters includes a shaft portion having a spine wire or stiffening element disposed within the lumen of a polymeric tube. The spine wire can be formed of metal and have alternating wide and narrow portions formed of wide and narrow segments. The wide segments can approach or preferably touch the inside wall of the outer polymeric tube. The wide segments can contribute to shaft stiffness by their length and by the inter-segment distance between segments. One shaft includes a spine wire having substantially constant inter-segment distance. Another shaft includes a spine wire having distally increasing inter-segment distances, contributing to distally increasing flexibility.

One group of catheters incorporating the present invention has a fluid pathway formed within the outer polymeric tube. Catheters in this group can have alternating narrow and wide segments, with apertures or openings formed around or through the wide segments. One group of wide segments have openings or apertures formed between portions of the segments and the outer tube wall. One group of segments has apertures formed through the segments. Openings through or around the wide segments allow fluid flow through or past the wide segments, which could otherwise block or greatly inhibit fluid flow.

Catheter shafts having openings through the wide segments can be used to deliver fluid. One such fluid delivery catheter is a dye delivery catheter used to deliver radiopaque contour media for angiography. Other catheters incorporating the present invention are angioplasty catheters, which can use the tubular shaft containing the spine wire as an inflation tube for delivery of balloon inflation fluid.

BRIEF DESCRIPTION OF THE DRAWINGS

FIG. 1 is a longitudinal, cross-sectional view of an angioplasty balloon catheter having a distal guide wire lumen and a movable stiffening element disposed within an inflation lumen;

FIG. 2 is a longitudinal, cross-sectional view of a proximal catheter shaft region including a stiffening element or spine wire having alternating wide and narrow regions disposed within an outer tube;

FIG. 3 is a transverse, cross-sectional view of one embodiment of a proximal catheter shaft taken through 3—3 in FIG. 2, having a tri-lobed profile;

FIG. 4 is a transverse, cross-sectional view of another embodiment of a proximal catheter shaft having a bi-lobed or hour-glass profile;

FIG. 5 is a transverse, cross-sectional view of another embodiment of a proximal catheter; and FIG. 6 is a transverse, cross-sectional view of another embodiment of a proximal catheter having a triangular profile.

DETAILED DESCRIPTION OF THE PREFERRED EMBODIMENTS

FIG. 1 illustrates a single operator exchange balloon angioplasty catheter 20 incorporating one aspect of the present invention. Catheter 20 includes generally a proximal region 22, a distal region 24, a manifold 26, a proximal outer tube 28 coupled to manifold 26, a distal outer tube 30 coupled to proximal outer tube 28, and an inflatable balloon 34 disposed on distal outer tube 30. Catheter 20 also includes a distal inner tube 32, which is inserted into and disposed within distal outer tube 30. Distal inner tube 32 has a lumen 38 within and can serve as a guide wire lumen. Proximal outer tube 28 and distal outer tube 30 have an inflation lumen 36 within, with inflation lumen 36 being in fluid communication with the interior of balloon 34. In one embodiment, proximal outer tube 28 is formed of a relatively stiff polymeric material such as polyimide, while distal outer and inner tubes 30 and 32 are formed of polyethylene.

Disposed within inflation lumen 36 is a movable core wire 40. Movable core wire 40 is slidably disposed within the inflation lumen in the example illustrated, allowing the core wire to extend distally to a location near balloon 34. In a preferred embodiment, a proximal pressure seal 42 is disposed about core wire 40 and secured to a proximal portion of manifold 26, forming a tight seal about core wire 40. Pressure seal 42 can serve to maintain inflation fluid pressure within inflation lumen 36 while core wire 40 remains disposed within the inflation lumen.

Core wire 40 is preferably tapered distally, having a smaller profile in the distal region than in the proximal region. Distally tapering the core wire can contribute to having a more flexible and smaller profile catheter in the catheter distal region. Continuously tapering the core wire over much of its length can provide increasing flexibility over much of its length. Core wire 40 preferably has a rounded distal tip 44 or other safety tip configuration. Core wire 40 is formed of Nitinol in one embodiment, and stainless steel in another embodiment. While a metallic core wire is preferred, other embodiments have elongate stiffening elements formed of polymeric materials, which can also provide stiffness.

In use, core wire 40 can be distally inserted within catheter 20 and catheter 20 inserted within the vasculature of a patient. In a preferred method, core wire 40 is inserted to the maximum desired distal extend prior to inserting catheter 20 within a patient. This can provide a maximum stiffness prior to inserting the catheter into the patient. The catheter can then be advanced within the patient's blood vessels. The core wire may lie within a distal portion of the catheter, initially in part to support the catheter distal region against buckling. In one method, core wire 40 is retracted relative to catheter 20 when the distal portion of the catheter is advanced into regions where greater flexibility is desired. In one method, core wire 40 is held in position while catheter 20 is advanced distally past the core wire. Even when partially proximally retracted, core wire 40 can provide pushability to the catheter, leaving only a catheter distal region without the added support of the core wire. In one method, the catheter distal portion having the core wire retracted is insinuated into vessels requiring the added flexibility of the catheter distal portion given by the core wire retraction. After the catheter distal portion is in position, the core wire can be advanced distally, providing support for further catheter advancement. This process can be repeated multiple times to properly position the catheter distal portion.

Once in position, the core wire is left in place in one embodiment, and inflation fluid injected into the inflation lumen around the core wire. In this method, the core wire can remain in place during the entire angioplasty procedure. In another method, the core wire can be removed substantially or entirely from the catheter prior to inflation of the balloon. In this method, the core wire can be advanced again after inflation, if desired. This method takes advantage of the fact that the added stiffening properties of the core wire may not be needed once the catheter is in position and no longer being advanced. Catheters taking advantage of this fact may be constructed having thinner walls and smaller profiles. In particular, catheters may be constructed incorporating the present invention which are not expected to be advanceable within the vasculature without the aid of an inserted core wire.

Referring now to FIG. 2, another catheter 120 is illustrated, including a proximal region 122 having a proximal shaft region 124. Catheter 120 includes a proximal manifold 126 and a distal guide wire tube 128. Proximal shaft 124 includes an outer tube 130 having an inner wall 131 containing an inner stiffening element or spine wire 132. In one embodiment, spine wire 132 includes an elongate distal portion 133, which can extend into a distal portion of the catheter. In the embodiment illustrated, spine wire distal portion 133 is distally tapered and extends near guide wire tube 128. Spine wire 132 can include a plurality of narrow regions, such as 134 and 136, and a plurality of wide regions or segments 138 and 140. In an alternate embodiment, the Spine wire has essentially a single wide segment such as wide segment 138, with no interspersed narrow segments. The terms "narrow" and "wide" refer generally to the maximum spine wire extent when viewed in transverse cross section. The spine wire narrow regions typically have a smaller cross-sectional profile or cross-sectional area relative to the wide regions. The wide regions can approach and typically are in contact with outer tube inside wall 131. The wide regions provide stiffness and support to the catheter shaft while the narrow regions provide flexibility.

Wide regions are separated by an inter-segment distance as indicated at "D1". D1 is a measure of the inter-segment distance measured from segment center-to-center. The inter-segment distance can also be measured by the length of the narrow region separating the wide regions, as indicated at "D2". The degree of stiffness of the shaft can be increased both by increasing the length of the wide regions and by decreasing the inter-segment distance between wide regions. In one embodiment, both the wide region length and the inter-segment distance are substantially constant over the shaft length. In another embodiment, the wide region length remains substantially constant while the inter-segment distance increases distally over a substantial portion of the shaft length. Increasing the inter-segment distance distally can provide increasing flexibility distally over the shaft length. In yet another embodiment, the wide region length is decreased distally. In still another embodiment, inter-segment distance is increased distally and wide region length is decreased distally, providing distally increasing flexibility. In some embodiments, proximal shaft 124 includes open or un-occluded regions 144 and 145, allowing fluid flow therethrough. Open regions 144 and 145 can be formed from fluted regions disposed on the periphery of the wide spine wire regions. In embodiments allowing such fluid flow, wide regions 140 are configured to allow fluid flow through the wide regions as well. In such embodiments, open regions can effectively function as inflation or dye delivery lumens.

Referring now to FIG. 3, one wide region 150 is illustrated in transverse cross section. Wide region 150 has three lobes 152 creating a tri-lobed profile contacting outer tube 130 in three locations. An open area through wide region 150 is formed by three openings or apertures 146 through the body of the spine wire. As used herein, apertures refer to openings either around or through the wide regions of the spine wire relative to what could otherwise be a solid, circular central member occluding the lumen of the outer tube. The outer extent of lobes 152 can provide stiffness or rigidity where contacting outer tube 130.

Referring now to FIGS. 4–6, other shaped wide regions are illustrated. FIG. 4 illustrates a wide region having a bi-lobed or hour-glass profile 154 and two apertures 156 through the wide region. FIG. 5 illustrates another profile 162 including a central member 164 and peripheral members 166 attached thereto. Peripheral members 166 form a series of apertures 168 between the members. FIG. 6 illustrates a triangular profile 158 having three apertures 160 allowing fluid flow past the spine wire wide regions.

The spine wire or stiffening member, such as member 132 in FIG. 2, can be manufactured using various techniques. In one method, a metallic wire is drawn through a releasable die for a length corresponding to the length of the narrow segment. The die is released or opened, a wide segment allowed to pass, the die closed again, and the next narrow segment formed by drawing through the die. To provide for fluid flow through the final shaft product, the wide segments can be formed in non-circular shapes or in less than perfect circular shapes. To form these non-circular shapes, the wire stock used initially can have a non-circular shape such as a triangle, a bi-lobed hourglass shape, tri-lobed shape, or a generally fluted outer surface. The wire stock can be drawn through a circular die to form the narrow sections, and the die released, allowing the non-circular shapes to retain shapes related to the original shapes.

In another method, the stiffening element can be manufactured by centerless grinding. Portions of the wire corresponding to the narrow segments can be ground down to the desired width or diameter. In this method, the beginning stock can have a non-circular shape, for example, the triangular, bi-lobed, or tri-lobed shapes previously mentioned. In yet another method, a central core element can be used to form the narrow regions and separate elements affixed to the central member to form the wide regions. For example, elements having central apertures can have non-circular shapes slip fit over the central member and further secured. For example, individual pieces or members can be affixed to the central element, thereby creating a wide element, leaving apertures or passages through the wide element. FIG. 5 illustrates one embodiment including a central element having peripheral members disposed about the central element which applicants believe suitable for manufacture by affixing members about a central core wire.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A catheter shaft comprising:

a tube having a lumen therethrough;

an elongate stiffening member disposed within said tube lumen, said stiffening member including a plurality of alternating wide and narrow segments, said segments having a cross-sectional area, wherein said wide segments have a larger cross-sectional area than said narrow segments wherein said narrow segments and said wide segments have solid cross sections, wherein said wide segments have said solid cross section over a length and wherein a substantial portion of said wide segments contact an interior surface of the tube; and a guidewire tube proximate to said tube lumen, the guidewire tube defining a guidewire lumen having a proximal guidewire port, where the elongate stiffening member extends distally beyond the proximal guidewire port.

2. A catheter shaft as recited in claim 1, wherein said wide segments have a cross-sectional profile not completely occluding said tube lumen, such that fluid flow through said plurality of wide segments within said tube is possible.

3. A tubular catheter shaft as recited in claim 1, wherein said wide segments have distally increasing inter-segment distance.

4. A catheter shaft comprising:

an tube having a lumen therethrough;

an elongate stiffening member disposed within said tube lumen, said stiffening member including a plurality of alternating wide and narrow segments, said segments having a cross-sectional area, wherein said wide segments have a larger cross-sectional area than said narrow segments wherein said narrow segments and said wide segments have a solid cross sections, wherein said wide segment have said solid cross section over a length; and a guidewire tube proximate to said tube lumen, the guidewire tube defining a guidewire lumen having a proximal guidewire port, where the elongate stiffening member extends distally beyond the proximal guidewire port;

wherein said wide segments have cross-sectional profiles having at least one aperture therethrough, the aperture having surfaces, such that fluid flow is possible through said segment within said outer tube, wherein said aperture surfaces together with the outer tube form a channel.

5. A tubular catheter shaft comprising:

a tube having a lumen therethrough;

an elongate stiffening member disposed within said tube lumen, said stiffening member including a plurality of alternating wide and narrow segments, said segments having a cross-sectional area, wherein said wide segments have a larger cross-sectional area than said narrow segments wherein said narrow segments and said wide segments have a solid cross sections, wherein said wide segment have said solid cross section over a length; and a guidewire tube proximate to said tube lumen, the guidewire tube defining a guidewire lumen having a proximal guidewire port, where the elongate stiffening member extends distally beyond the proximal guidewire port;

wherein said wide segments have cross-sectional profiles having at least two apertures therethrough.

6. A catheter shaft, comprising:

a tube having a lumen therethrough;

an elongate stiffening member disposed within said tube lumen, said stiffening member including a plurality of alternating wide and narrow segments, said segments having a cross-sectional area, wherein said wide segments have a larger cross-sectional area than said narrow segments, wherein said wide segments have said solid cross section over a length, and wherein a substantial portion of said wide segments contacts an interior surface of the tube; and a guidewire tube proximate to said tube lumen, the guidewire tube defining a guidewire lumen having a proximal guidewire port, where the elongate stiffening member extends distally beyond the proximal guidewire port.

7. A catheter shaft as recited in claim 6, wherein said wide segments have a cross-sectional profile not completely occluding said tube lumen, such that fluid flow through said plurality of wide segments within said tube is possible.

8. The catheter shaft of claim 6, wherein said wide segments have a circular cross-sectional profile.

9. A catheter shaft, comprising:

a first elongate member having a proximal opening, a distal end and a lumen extending between the proximal opening and the distal end;

a second elongate member disposed within said first elongate member lumen, said second elongate member including a plurality of alternating wide and narrow segments, said segments having a cross-sectional area, wherein said wide segments have a larger cross-sectional area than said narrow segments wherein said narrow segments and said wide segments have solid cross sections, wherein said wide segments have said solid cross section over a length and wherein a substantial portion of said wide segments contact an interior surface of the first elongate member; and a guidewire tube proximate to said tube lumen, the guidewire tube defining a guidewire lumen having a proximal guidewire port, where the elongate stiffening member extends distally beyond the proximal guidewire port.

10. A catheter shaft, comprising:

a first elongate member having a proximal opening, a distal end and a lumen extending between the proximal opening and the distal end; and an elongate stiffening member disposed within said first elongate member lumen, said stiffening member including a first narrow segment;
a first wide segment distal the first narrow segment;
a second narrow segment distal the first wide segment; and
a second wide segment distal the second narrow segment; and a guidewire tube proximate to said tube lumen, the guidewire tube defining a guidewire lumen having a proximal guidewire port, where the elongate stiffening member extends distally beyond the proximal guidewire port;

wherein said first and second wide segments have a larger cross-sectional area than said first and second narrow segments wherein said first and second narrow segments and said first and second wide segments have solid cross sections, wherein said first and second wide segments have said solid cross section over a length and wherein a substantial portion of said first and second wide segments contact an interior surface of the first elongate member.

11. The catheter shaft of claim 10, wherein the elongate stiffening member comprises stainless steel.

12. The catheter shaft of claim 10, wherein the first elongate member comprises a polymeric material.

13. A catheter shaft, comprising:

a tube having a lumen therethrough and a proximal end; and an elongate stiffening member having a proximal end disposed within said tube lumen, said stiffening member including a plurality of alternating wide and narrow segments, said segments having a cross-sectional area, wherein said wide segments have a larger cross-sectional area than said narrow segments, wherein said wide segments have said solid cross section over a length; wherein the proximal end of the tube is distal the proximal end of the stiffening member; and a guidewire tube proximate to said tube lumen, the guidewire tube defining a guidewire lumen having a proximal guidewire port, where the elongate stiffening member extends distally beyond the proximal guidewire port.

14. The catheter shaft of claim 13, wherein the tube comprises a distal end and the elongate stiffening member comprises a distal end, and wherein the distal end of the elongate member is proximal the distal end of the tube.

15. A catheter shaft, comprising:

a tube having a lumen therethrough; and an elongate stiffening member disposed within said tube lumen, said stiffening member including a plurality of alternating wide and narrow segments, said segments having a cross-sectional area, wherein said wide segments have a larger cross-sectional area than said narrow segments wherein said narrow segments and said wide segments have a solid cross sections, wherein said wide segments have said solid cross section over a length and wherein a substantial portion of said wide segments supports an interior surface of the tube; and a guidewire tube proximate to said tube lumen, the guidewire tube defining a guidewire lumen having a proximal guidewire port, where the elongate stiffening member extends distally beyond the proximal guidewire port.

16. A catheter shaft, comprising:

a tube having a lumen therethrough;

an elongate stiffening member disposed within said tube lumen, said stiffening member including a plurality of alternating wide and narrow segments, said segments having a cross-sectional area, wherein said wide segments have a larger cross-sectional area than said narrow segments, wherein said wide segments have said solid cross section over a length and wherein at least a one wide segment contacts an interior surface of the tube over a portion of its length; and a guidewire tube proximate to said tube lumen, the guidewire tube defining a guidewire lumen having a proximal guidewire port, where the elongate stiffening member extends distally beyond the proximal guidewire port.

17. A method for advancing a catheter having a lumen, comprising:

providing said catheter having a first lumen and a second lumen;

providing an elongate stiffening member having a plurality of alternating wide and narrow segments, said segments having a cross-sectional area, wherein said wide segments have a larger cross-sectional area than said narrow segments wherein said narrow segments and said wide segments have a solid cross sections, wherein said wide segments have said solid cross section over a length;

providing a guidewire;

advancing the guidewire through a vessel to a target distal region;

advancing said stiffening member distally through said second catheter lumen, wherein a substantial portion of said wide segments contact an interior surface of the catheter;

threading said guidewire through said first lumen;

advancing said catheter distally into said vessel over said guidewire; and moving said stiffening member proximally.

18. A method for advancing a catheter having a lumen, comprising:

providing said catheter having a first lumen and a second lumen;

providing an elongate stiffening member having a plurality of alternating wide and narrow segments, said segments having a cross-sectional area, wherein said wide segments have a larger cross-sectional area than said narrow segments wherein said narrow segments and said wide segments have a solid cross sections, wherein said wide segments have said solid cross section over a length disposed in said second catheter lumen, wherein a substantial portion of said wide segments contact an interior surface of the catheter;

providing a guidewire;

advancing the guidewire through a vessel to a target distal region;

threading said guidewire through said first lumen; and advancing said catheter distally into said vessel over said guidewire.

* * * * *